United States Patent [19]

Knollenberg

[11] Patent Number: 4,728,190
[45] Date of Patent: Mar. 1, 1988

[54] DEVICE AND METHOD FOR OPTICALLY DETECTING PARTICLES IN A FLUID

[75] Inventor: Robert G. Knollenberg, Boulder, Colo.

[73] Assignee: Particle Measuring Systems, Inc., Boulder, Colo.

[21] Appl. No.: 787,602

[22] Filed: Oct. 15, 1985

[51] Int. Cl.⁴ .............................................. G01N 21/00
[52] U.S. Cl. ................................... 356/336; 356/338; 250/574
[58] Field of Search ...................... 356/336, 338, 343; 250/576, 574, 239

[56] References Cited

U.S. PATENT DOCUMENTS 4,616,927 10/1986 Phillips et al. .................. 356/338 X

FOREIGN PATENT DOCUMENTS 3338351 5/1984 Fed. Rep. of Germany ...... 356/338

OTHER PUBLICATIONS

"'In Situ' Optical Particle Size Measurements In Liquid Media" by Robert G. Knollenberg, Proceedings of Pure Water Conference, Palo Alto, Calif., Jan. 13-14, 1983.

Primary Examiner—Eugene R. Laroche
Assistant Examiner—Robert J. Pascal
Attorney, Agent, or Firm—Robert E. Harris

[57] ABSTRACT

A device and method are disclosed for optically detecting particles in a fluid. A fluid passage with transparent walls defining a monitoring volume, or region, is provided, and particles in the fluid are optically detected by directing a laser beam through the fluid in the monitoring region and collecting light scattered by the particles. A capillary is utilized as the fluid passage, and reflections from the walls of the capillary are effectively precluded. The laser beam is directed through the capillary by means of a window at the entrance side and a lens at the collecting side with the air-glass interfaces being outside the depth of view of particle monitoring within the monitoring region. As a result of this arrangement, the amount of scattered light is greatly reduced and a more uniform light signal is achieved which results in better size resolution of particles than has heretofore been achieved.

20 Claims, 8 Drawing Figures

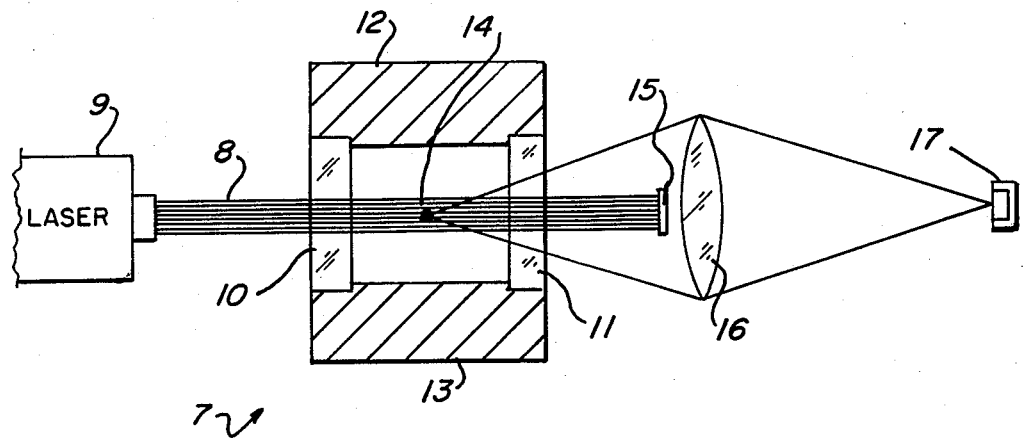
Fig_1
PRIOR ART
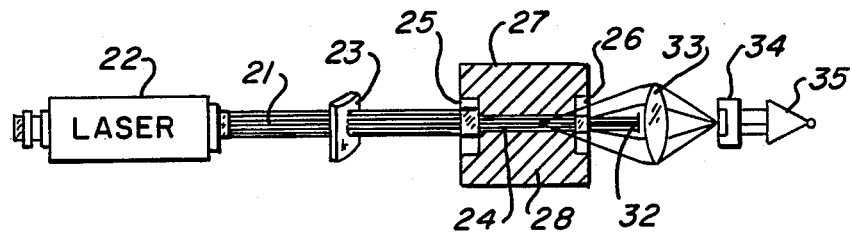
Fig_2A
PRIOR ART
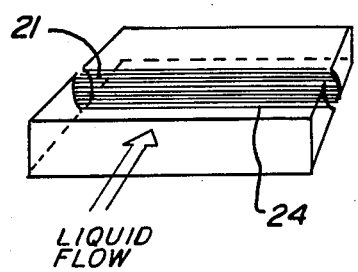
Fig_2B
PRIOR ART

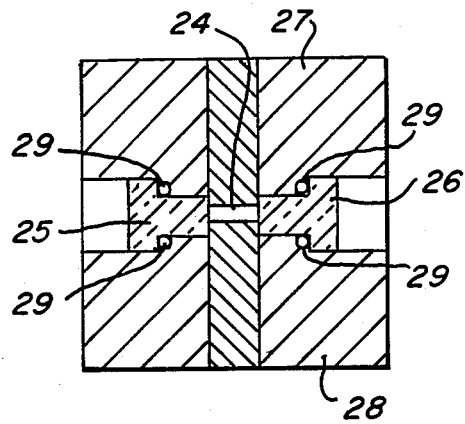
Fig_2C
PRIOR ART
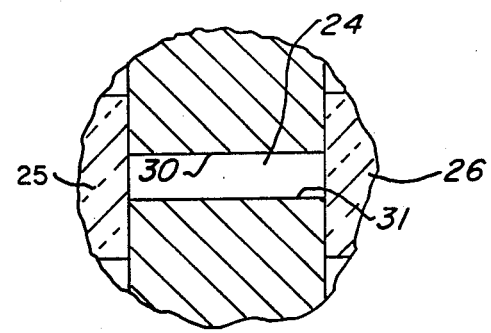
Fig_2D
PRIOR ART
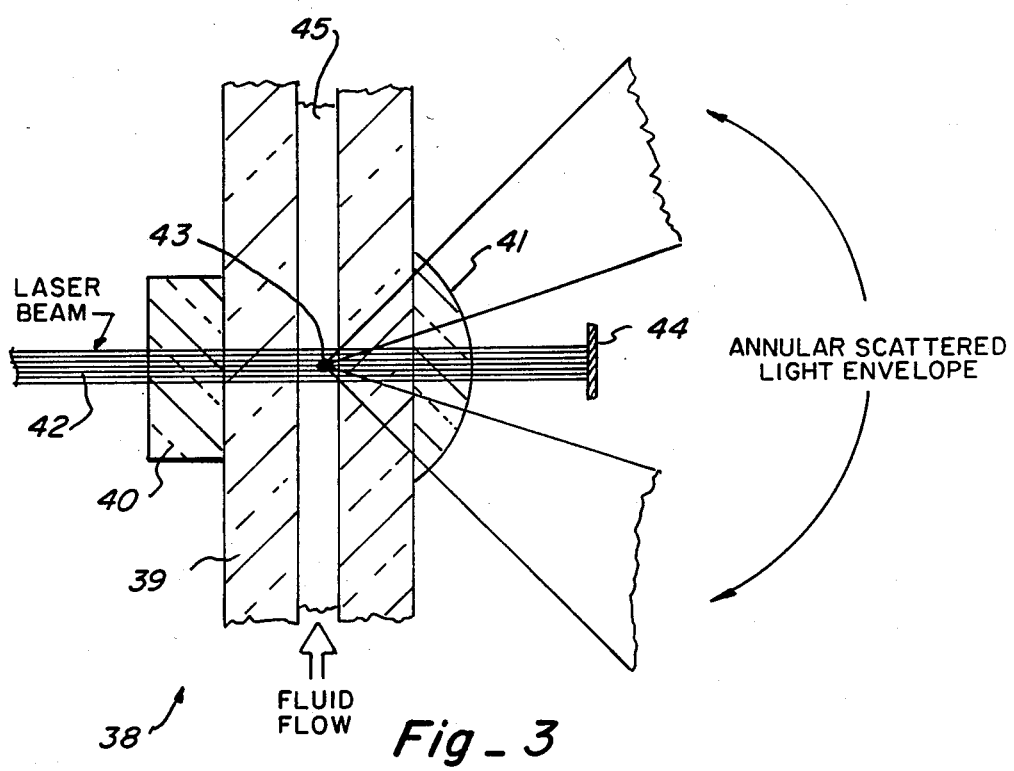
Fig_3

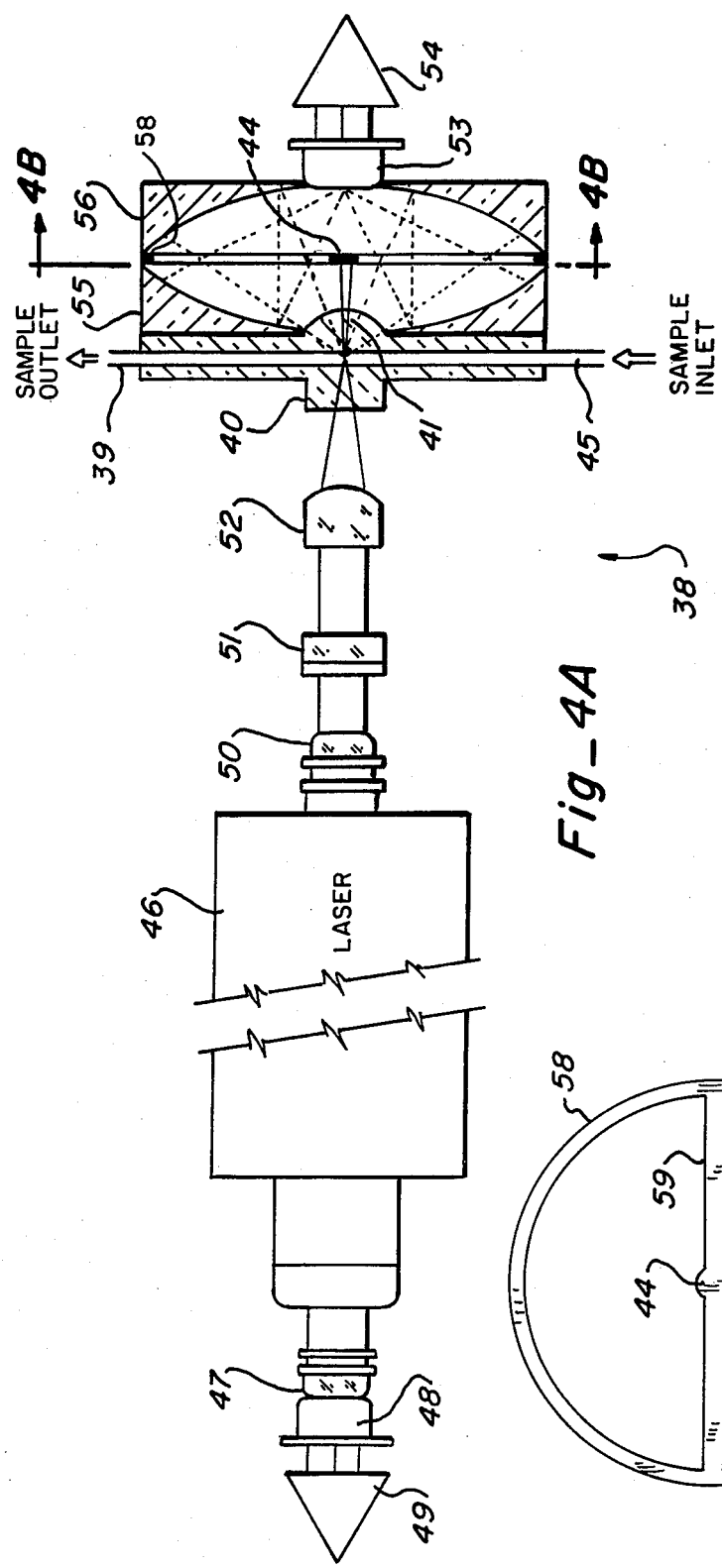
Fig_4A
Fig_4B

DEVICE AND METHOD FOR OPTICALLY DETECTING PARTICLES IN A FLUID

FIELD OF THE INVENTION

This invention relates to optical detectors, and, more particularly, relates to optical detection of particles in a fluid.

BACKGROUND OF THE INVENTION

The detection and/or measurement of particles in a fluid has become increasingly important over the past few years, and devices and methods have heretofore been suggested and/or utilized for achieving such detection and/or measurement.

More recently, particle detectors utilizing lasers have been suggested for use in detection and/or measurement, including particle sizing (see, for example, U.S. Pat. No. 3,406,289 and the following articles: R. G. Knollenberg, "An Active Scattering Aerosol Spectrometer", Atmospheric Technology, Number 2, June, 1973, pages 80–81; R. G. Knollenberg, "Active Scattering Aerosol Spectrometry", Dental Bureau of Standards Special Publication 412, issued October, 1974, pages 57–64; R. G. Knollenberg and R. E. Leuhr, "Open Cavity Laser 'Active' Scattering Particle Spectrometry From 0.05 to 5 Microns", Fine Particles, Aerosol, Generation Measurement, Sampling and Analysis, Editor Benjamin Y. H. Liu, Academic Press, May, 1975, pages 669–696; R. G. Knollenberg, "Three New Instruments For Cloud Physics Measurement: The 2-D Spectrometer, the Forward Scattering Spectrometer Probe, and the Active Scattering Aerosol Spectrometer", American Meterological Society, International Conference on Cloud Physics, July, 1976, pages 554–561; and R. G. Knollenberg, "The Use of Low Power Lasers in Particle Size Spectrometry", Proceedings of the Society of Photo-Optical Instrumentation Engineers: Practical Applications of Low Power Lasers, Volume 92, August, 1976, pages 137–152.

The detection and/or measurement of particles suspended in a liquid media is of tremendous importance, for example, to the semiconductor and related electronic component industries since such particles have been found to constitute a level of microcontamination sufficient to reduce manufacturing yields to an unprofitable level. Typical process liquids used in these industries include deionized water, photoresists, strong acids and bases, hydrocarbon solvents and proprietary mixtures of chemicals.

Instruments that are currently used to monitor contaminates within such process liquids are largely optical using light scattering to size particles, and these instruments can be categorized as belonging to one of two possible classes—"in-situ" instruments that measure remotely and sample a small portion of the total fluid volume utilized, and "volumetric" instruments that sample all of the fluid volume utilized (a discussion of in-situ and volumetric instruments can be found in "'In situ' Optical Particle Size Measurements in Liquid Media", by Robert G. Knollenberg, Proceedings of Pure Water Conference, Palo Alto, Calif. Jan. 13–14, 1983).

Both the in-situ and volumetric instruments have characteristics which allow them to be optimally used under different circumstances. Both types of these presently known instruments, however, can logically view only a small illuminated volume if maximum sensitivity is desired (as is required for microcontamination measurements, for example).

A volumetric instrument must have a highly restricted passage to allow all of the fluid to pass through the illuminated view or monitoring region. Typical dimensions of such a passage to provide the necessary restriction are on the order of one millimeter diameter to thereby enable maximum fluid flows of 100 to 200 ml/min.

An in-situ instrument, on the other hand, while having no required flow restrictions (since only a small portion of the fluid is sampled), is nevertheless presently restricted in viewing volume by established optical parameters (field-of-view, depth-of-field, etc.) rather than by physical boundaries.

Heretofore, in-situ instruments have exhibited superior performance characteristics as compared with known volumetric instruments. One reason for this is that known volumetric instruments have required interfaces between the fluid and the fluid confining vessel walls and such interfaces are sources of large amounts of stray light. This stray light establishes a noise background level from which light scattered by individual particles must be differentiated. Obviously, if the noise background is greater than the particle scattering signal, the particles within the fluid cannot be detected or measured. With in-situ type instruments, the particles are illuminated and viewed through windows whose fluid interfaces can be removed far enough away from the illuminated view-volume (monitoring region) to be out of the depth-of-field and the light scattering noise contribution has therefore been of a negligible nature.

Thus, known in-situ and volumetric instruments, while having been found to be useful, nevertheless have not been found to be fully satisfactory, and further improvements therein would therefore be found useful.

SUMMARY OF THE INVENTION

This invention provides an improved device and method for optically detecting particles in a fluid. In essence, an improved volumetric type device has been achieved that incorporates advantageous functions heretofore found only in in-situ type devices, including minimizing interfacial stray light. As a result, an improved device has been realized that minimizes background noise, due to the presence of stray light, and provides a more uniform light signal, without multiple reflections, with the device achieving better size resolution than has heretofore been possible.

It is therefore an object of this invention to provide an improved device and method for optically detecting particles in a fluid.

It is another object of this invention to provide an improved device and method for optically detecting particles in a fluid by minimizing background noise due to stray light.

It is another object of this invention to provide an improved device and method for optically detecting particles in a fluid that provides more uniform light signals.

It is still another object of this invention to provide an improved device and method for optically detecting particles in a fluid with reflections at a monitoring region being effectively precluded.

It is still another object of this invention to provide an improved device and method for optically detecting particles in a fluid that provides better size resolution than has heretofore been achieved.

With these and other objects in view, which will become apparent to one skilled in the art as the description proceeds, this invention resides in the novel construction, combination, arrangement of parts and method substantially as hereinafter described and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which:

FIG. 1 is a simplified illustration of a typical known in-situ type instrument;

FIG. 2A is a simplified illustration of a typical known volumetric type instrument;

FIG. 2B is a partial perspective view illustrating the monitoring region of the volumetric type instrument shown in FIG. 2A;

FIG. 2C is a cut-away side view of a volumetric instrument such as shown in FIG. 2A and illustrating typical component requirements;

FIG. 2D is an expanded view of the monitoring region as shown for volumetric type instrument of FIG. 2C and illustrating the required reflective surfaces thereat;

FIG. 3 is a partial cut-away side view illustrating the device of this invention using a capillary and window and lens arrangement;

FIG. 4A is a simplified side view (partially in cut-away) illustrating the device of this invention as shown in FIG. 3; and FIG. 4B is a sectional view taken through lines 4B—4B of FIG. 4A and illustrating the light trap mask utilized in the device of this invention as shown in FIG. 4A.

DESCRIPTION OF THE INVENTION

This invention achieves desirable features of known in-situ type instruments, shown typically in FIG. 1, and is based upon known volumetric type instruments, shown typically in FIG. 2, to thereby achieve an improved device that has desirable features of both. By so doing, the device of this invention, as shown in FIGS. 3 and 4, reduces background light by a factor of nearly 100× below that of known devices of these types which allows the lower limit of sizing to be extended from about 0.5 microns to about 0.3 microns (the ratio of scattering signals for 0.5 and 0.3 microns is approximately a factor of 10).

As shown in FIG. 1, a typical known in-situ instrument 7 requires that laser beam 8 from laser beam generating unit 9 be directed through a pair of spaced windows 10 and 11 mounted in blocks 12 and 13 so that laser beam 8 passes through monitoring region 14, which monitoring region is adapted to receive a liquid that is caused to flow through the laser beam while at the monitoring region. The direct beam is trapped at direct beam light trap 15 after passing through the monitoring region, while scattered light (i.e., light scattered by particles in the liquid at the monitoring region) is directed by collecting lens 16 through a photodiode 17 for developing thereat an electrical signal indicative of the collected scattered light.

As brought out above, while known in-situ type instruments can have windows with fluid interfaces removed far enough to be out of the depth-of-field of the viewed volume (as can the other walls as indicated in FIG. 1), such instruments are limited to remote measurement with sampling being achieved with respect to only a small portion of the total fluid volume to be utilized.

As shown in FIG. 2A, a typical known volumetric type instrument 20 requires that laser beam 21 from laser beam generator unit 22 (typically an AG-NE laser) be passed through cylinder lens 23 and then directed through monitoring region 24 (as shown more fully in FIG. 2B) by means of windows 25 and 26 mounted in blocks 27 and 28.

As shown in FIG. 2C, the known volumetric type sampling cell is typically formed by use of four metal plates forming blocks 27 and 28. The sandwiched metal parts can be either accurately lapped, sealed with gaskets, or cemented to obtain leak-free assemblies, and the windows can either be sealed by the use of o-rings (as indicated by o-rings 29 in FIG. 2C) or cemented.

The volumetric cell assembly requires that surfaces 30 and 31 (as shown more fully in FIG. 2D) be reflective so that the light scattered by particles near the far side of the flow cross-section is multiply reflected so as to be collected with approximately the same efficiency as a particle near the near side of the flow cross-section.

In the volumetric type instrument as shown in FIG. 2A, the direct light from laser beam 21 is typically trapped at light trap 32, while light, scattered by particles in the liquid, is directed by collecting lens 33 to photodiode 34, which photodiode provides an electrical signal that is coupled to preamplifier 35, the output of which preamplifier is indicative of a predetermined parameter (such as size) of detected particles in the liquid.

In the device 38 of this invention, as shown in FIGS. 3 and 4, three optical glass parts are utilized—a capillary 39 (which capillary has transparent walls and may have either a rectangular or a circular bore), a window 40, and a lens 41.

With particular respect to FIG. 3, laser beam 42 is directed through window 40 to monitoring region 43, with the direct beam passing through lens 41 being trapped at direct beam light trap 44. The fluid to be monitored is directed through passage 45 within capillary 39, and all interfaces are glass-fluid. As a functional assembly, an integrated micro-optical cell results.

Typically, the laser unit (as shown in FIG. 4A) includes a laser generating tube 46 as the source of illumination with the resulting laser beam being astigmatically focused to cover the capillary cross-section as a thin cross-section of illumination.

As also indicated in FIG. 4A, the laser unit also conventionally includes laser mirror 47, reference photodiode 48 and reference preamplifier 49 at one end, and laser mirror 50 and condensing lenses 51 and 52 at the other end supplying the laser beam 42 to the monitoring cell. Mask (light trap) 44 is dimensioned to block (and absorb) all directly transmitted light passing through the monitoring region without appreciably reducing the collectable scattered light.

Light scattered by the particles in the fluid within passage 45 of capillary 39 at monitoring region 43 is collected and becomes the signal for particle size analysis, which signal, as also shown in FIG. 4A, is directed to photodiode 53, the output of which is coupled to signal preamplifier 54. While not specifically shown, it is to be appreciated that the output signal from preamplifier 54 is coupled to a utilization device capable, for example, of display or storage. For use in particle sizing, the exact particle size scattering signal relationship can either be determined theoretically or empirically using particles of known size.

The function of entrance window 40 is to move the entrance glass-air interface away from the centrally viewed volume of the capillary, and this window can be as thick as necessary. Exit lens 41 has the same function as does entrance window 40, and, in addition, has a uniform curvature the constant radius of which is measured from the center of the "view-volume" which allows the rays illuminating from the scattering particles to be undeviated when passing through the glass-air interface upon exiting the lens so that the particles appear to be in the same position as if the glass was absent.

The scattered light exiting from lens 41 is in the form of an annular scattered light envelope that can be collected by a variety of optical systems, but, for maximum collection, it has been found that a parabolic mirror pair (formed by facing parabolic mirrors 55 and 56, as shown in FIG. 4A, at 1:1 conjugates) can be used to good advantage. This optical system for collecting scattered light generates a large solid angle and the necessary mask 44 used to block transmitted light can be conveniently positioned between the mirrors.

As shown in FIG. 4B, a structure 57 is provided which includes a support band 58 for supporting mask 44, which mask includes opaque strips 59 which extend from band 58 to an enlarged opaque center portion 60. When mask 44 is positioned between mirrors 55 and 56, as shown in FIG. 4A, band 58 is sandwiched between the mirror edges, center portion 60 collects transmitted light, and strips 59 collect defracted light generated by the capillary inside edges with mask 44 being oriented orthogonal to the capillary axis. Cylinder lenses 51 and 52 are preferably used to generate the desired illumination beam shaping.

The fluid-glass interface produces a reflective loss calculated according to the well known Fresnal formula:

$$\text{Reflectivity} = \left( \frac{n_{G1} - n_{G2}}{n_{G1} + n_{F1}} \right)^2$$

Where $n_{G1}$ is the refractive index of glass and $n_{F1}$ is the fluid refractive index. The reflection losses become equal to 0 when the fluid and glass interfaces are equal, but are also extremely small in nearly all cases for common liquids (where the range of n is approximately 1.3 to 1.5 for the fluid and where n equals 1.45 to 1.55 for the glass).

The device of this invention thus provides an advantage over known devices wherein the metals used have extremely high reflectivities. In general, the scattering losses occurring at interfaces are also proportional to the index contrast between the fluid and confining vessel walls. This means that a small glass imperfection at a fluid interface will scatter much less light than will an identical defect (in size and shape) in a metal interface with the same fluid. In fact, if the two materials in an interface have identical refractive indices, such imperfections would produce no scattering.

In the device of this invention, light scattering due to particle presence in the liquid can be observed directly at all points along the beam within the capillary cross-section without the need for multiple reflections to relay the scattered light as has heretofore been required by known cells. This results in a more uniform light signal scattered by particles in the fluid at all positions and better size resolution.

From the foregoing, it is to be appreciated that this invention provided an improved device and method for detection of particles in a fluid, with the device and method being particularly useful for particle sizing, with measurements made utilizing the device and method of this invention having produced a reduction in stray light by as much as a factor of 100× over known volumetric type devices.

What is claimed is:

1. A device for optically detecting particles in a fluid, said device comprising:
   light means for providing a light beam;
   fluid passage means for providing a fluid passage through a monitoring region, said fluid passage means being substantially formed by transparent wall means at said monitoring region with said transparent wall means being effectively precluded from reflecting light within said monitoring region;
   light passage enabling means in the path of said light beam for permitting passage of said light beam through said fluid passage means in said monitoring region, said light passage enabling means providing interfaces that are outside the depth of field for detecting particles in a fluid within said fluid passage means at said monitoring region; and
   light collecting means for collecting light scattered by particles in said fluid within said fluid passage means at said monitoring region, said collecting means providing an output that is substantially free of light reflections at said monitoring region so that said output is effectively indicative of at least one predetermined parameter of said particles detected in said fluid.

2. The device of claim 1 wherein said light means includes means for generating a laser beam, and wherein said light passage enabling means directs said laser beam through said fluid passage means at said monitoring region.

3. The device of claim 1 wherein said fluid passage means includes a capillary providing said passage for fluid through said monitoring region.

4. The device of claim 3 wherein said light passage enable means includes a window and lens arrangement positioned adjacent to said capillary for directing light through said monitoring region in a predetermined path.

5. The device of claim 1 wherein said light collecting means includes signal generating means that provides an electrical signal indicative of collected light scattered by particles in said fluid at said monitoring region.

6. The device of claim 1 wherein said indicated parameter of particles at said monitoring region is particle size, and wherein said device provides an output indication of sizing having high resolution.

7. A device for optically detecting particles in a fluid, said device comprising:
   laser means for providing a laser beam;
   fluid passage means for providing a fluid passage through a monitoring region, said fluid passage means being substantially formed by transparent wall means at said monitoring region with said transparent wall means being effectively precluded from reflecting light within said monitoring region;

light passage enabling means in the path of said laser beam for permitting passage of said laser beam through said fluid passage means in said monitoring region, said light passage enabling means providing interfaces that are outside the depth of field for detecting particles in fluid within said fluid passage means at said monitoring region; and collecting means for collecting light scattered by particles in said fluid within said fluid passage means at said monitoring region, said collecting means providing an output that is substantially free of light reflections at said monitoring region so that said output is effectively indicative of at least one predetermined parameter of said particles detected in said fluid.

8. The device of claim 7 wherein said fluid passage means is formed by a capillary passing through said monitoring region.

9. The device of claim 7 wherein said light passage means is formed by a window and lens arrangement positioned in the path of said laser beam.

10. The device of claim 9 wherein said window is positioned in a path of said laser beam prior to said laser beam reaching said monitoring region and said lens is positioned in the path of light that is scattered during passage of said laser beam through said monitoring region.

11. The device of claim 7 wherein said collecting means includes mirror means and photodiode means.

12. A device for optically detecting particles in a fluid, said device comprising:

laser means for providing a laser beam;

a capillary for receiving fluid and providing a passage for said fluid through a monitoring region;

a window adjacent to said capillary and in the path of said laser beam to enable said laser beam to be directed through said capillary at said monitoring region so that particles in said fluid scatter light at said monitoring region with light reflections due to said capillary being substantially precluded;

a lens adjacent to said capillary and in the path of light scattered by particles in said fluid within said capillary at said monitoring region, said lens enabling scattered light to exit from said capillary without appreciable reflection thereof;

a mirror means to collect said scattered light exiting from said capillary; and a photodiode for collecting said light collected by said mirror means, said photodiode providing an electrical output signal that is substantially free of light reflections due to said capillary so that said output signal is effectively indicative of a predetermined parameter of particles detected in said fluid at said monitoring region.

13. The device of claim 12 wherein said mirror means includes a pair of parabolic mirrors positioned adjacent to said lens.

14. The device of claim 12 wherein said window, capillary and lens minimize stray light to thereby provide a more uniform light signal without appreciable non-particle light reflection within said monitoring region.

15. The device of claim 14 wherein said predetermined parameter of said particles is particle size, and wherein said resolution of particle size in enhanced.

16. The device of claim 15 wherein the lower limit of sizing is extended to about 0.3 microns.

17. The device of claim 15 wherein said resolution is enhanced by a factor of at least about 10.

18. A method for optically detecting particles in a fluid, said method comprising:

providing a passage through a monitoring region with the passage including substantially transparent walls within the monitoring region;

introducing a fluid into the provided passage;

directing light toward the monitoring region in a manner such that particles in the fluid within the passage scatter the light with light reflections due to the transparent walls of the passage being appreciably reduced;

collecting light scattered by particles in the fluid passing through the provided passage; and providing an output based upon the collected light scattered by the particles detected in the fluid within the passage at the monitoring region with said output being substantially free of light reflections due to said transparent walls at said monitoring region.

19. The method of claim 18 wherein said method includes generating a laser beam to provide said light to be directed toward said monitoring region, and providing a window and lens arrangement for directing the laser beam through the monitoring region and collecting light scattered by particles within the fluid in the monitoring region with the window and lens being outside the depth of field of the monitoring region.

20. The method of claim 19 wherein the method includes providing a capillary as the passage for the fluid, and positioning said capillary between the window and lens.

* * * * *